United States Patent [19]

Moore

[11] 4,213,699

[45] Jul. 22, 1980

[54] METHOD OF MEASURING LOW CONCENTRATIONS OF A LIGHT ABSORBING COMPONENT

[75] Inventor: Malcolm Moore, St-Denijs Westrem, Belgium

[73] Assignee: s.a. Texaco Belgium n.v., Brussels, Belgium

[21] Appl. No.: 661,917

[22] Filed: Feb. 27, 1976

[51] Int. Cl.$^2$ .................. G01N 33/28; G01N 21/00
[52] U.S. Cl. ........................... 356/70; 250/573; 356/436
[58] Field of Search ............. 356/70, 201, 208, 180, 356/184, 256, 409, 432, 436; 331/94.5 T; 350/179, 180; 250/564, 573

[56] References Cited

PUBLICATIONS

"Accurate and Sensitivity of the Thermal Lens Method for Measuring Absorption.", Solimini, Applied Optics, vol. 5 #12 pp. 1931-1939, Dec. 1966.

*Primary Examiner*—Vincent P. McGraw
*Attorney, Agent, or Firm*—Carl G. Ries; Robert A. Kulason; Henry C. Dearborn

[57] ABSTRACT

A laser beam is transmitted through a medium containing the component to be measured. The wavelength of the beam is such that it is absorbed by the component but not by the remainder of the medium. The divergence of the beam is measured to indicate a change in the index of refraction of the medium due to the absorption by the component.

10 Claims, 2 Drawing Figures

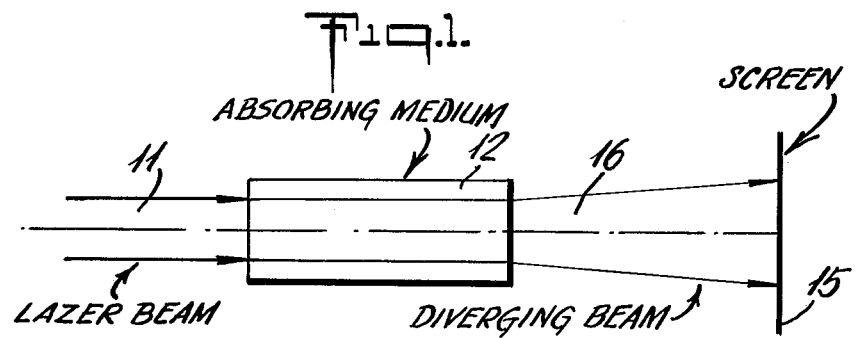
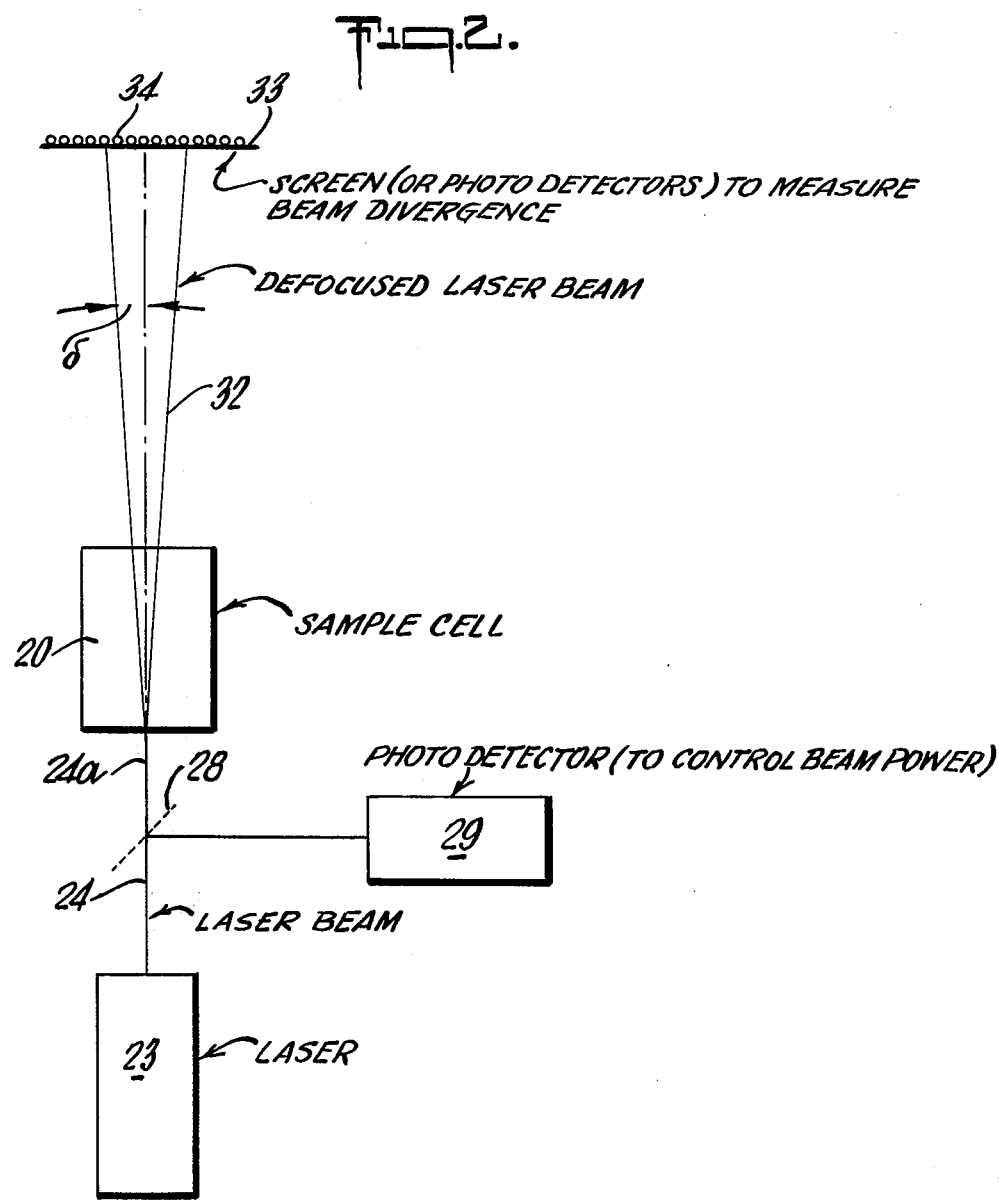

METHOD OF MEASURING LOW CONCENTRATIONS OF A LIGHT ABSORBING COMPONENT

BACKGROUND OF THE INVENTION

1. Field of the Invention

This invention concerns a method of measuring low concentrations of a light absorbing component in a transparent medium. More specifically, the method deals with measurement of a non-fluorescent component and especially the presence of oil in a mixture such as with water or the like.

2. Description of the Prior Art

While many techniques may be employed in making a determination concerning the presence of a particular component in a mixture and particularly a relatively transparent mixture, one of the more accurate prior techniques involved the absorption measurement of a range of wavelengths in a spectroscope for determining the presence of a particular component by measuring its absorption at a particular wavelength. However, a major failing of that technique becomes apparent in the case where there may be other factors that cause a reduced reading at the particular wavelength. Then it is not possible to distinguish between the presence of such other factors and the presence of the desired component.

Thus, it is an object of this invention to provide a method for measuring low concentrations of a component where a determination of optical divergence is made, that depends upon the absorption of a particular wavelength of the light beam employed.

SUMMARY OF THE INVENTION

Briefly, the invention concerns a method of measuring low concentrations of a light absorbing component in a transparent medium. It comprises the transmitting of a laser beam through said medium. The said beam has a wavelength that is absorbed by said component, and the method comprises determining the amount of divergence of said beam created by passage through said medium.

Again briefly, the invention concerns a method of measuring low concentrations in a fluid sample of crude oil dissolved in carbon tetrachloride, benzene and water. The method comprises transmitting a beam of laser light having a wavelength of 448.0 millimicrons. The said beam is directed vertically through said sample, and said beam is substantially cylindrical with a predetermined width. The method also comprises measuring the width of the image of said beam after passing through said sample, at a predetermined distance therefrom by scaling said image on a screen.

BRIEF DESCRIPTION OF THE DRAWINGS

The foregoing and other objects and benefits of the invention will be more fully set forth below in connection with the best mode contemplated by the inventor of carrying out the invention, and in connection with which there are illustrations provided in the drawings, wherein:

FIG. 1 is a schematic diagram illustrating the basic elements that are employed in carrying out a method according to the invention; and FIG. 2 is another schematic diagram illustrating a particular application of the method according to the invention in connection with a liquid medium and component thereof.

DESCRIPTION OF THE PREFERRED EMBODIMENT

Studies have shown that a beam of light passing through an absorbing medium has part of its absorbed energy converted into heat and the rest re-radiated as fluorescence. In connection with this invention it has been discovered that the foregoing properties may be employed by using a beam of single wavelength light which is passed through medium having a component that absorbs that wavelength. The beam will produce heating effects on the component of such medium and thus cause a change in its index of refraction. For most media the variation of refractive index is negative with temperature so that a diverging lens effect is created which defocuses the beam.

For example, referring to FIG. 1, there is shown a laser beam 11 that has a predetermined wavelength. Beam 11 is projected through an absorbing medium 12 and then produces an image on a screen 15. It will observed that the parallel sided, or columnar laser beam 11 is substantially cylindrical and is caused to diverge in passing through the absorbing medium 12 so that a diverging beam 16 is illustrated.

The laser beam 11 is one that has a radial intensity distribution that is maximum at the center and falls off smoothly with increasing radius. It may be well described by a Gaussian expression. With such a beam, the temperature distribution produced in the medium will also show a maximum along the beam axis and the same radial intensity distribution. However, this is only so (strictly speaking) for media in which the heat loss is solely by conduction. Consequently, the medium 12 illustrated would be a solid which illustrates the principles of the invention. Also, as mentioned above, since most media will show a negative variation of refractive index with temperature increase, it will be clear that the temperature distribution will produce a diverging lens in the medium and consequently will cause defocusing. Therefore the beam radius will be increased as indicated by the schematic illustration of beam 16 in FIG. 1.

In regard to solid materials and those media where the heat loss is predominantly by conduction, a theoretical treatment of the conditions leads to a simple relationship between the steady-state beam divergence and the absorption of the medium. Thus, for a beam with Gaussian intensity distribution the relationship is:

$$\theta = -\left(\frac{\partial n}{\partial T}\right) \frac{P}{\pi k a} 0.32 (1 - e^{-\alpha z}) \quad (1)$$

where $\theta$ is the half-angle divergence; $(\partial n/\partial T)$ is the change of refractive index with temperature; P is the beam power; k is the thermal conductivity; $\alpha$ is the absorption coefficient; z is the absorbing path length; and "a" is the beam radius measured at the $e^{-1}$ intensity point. Therefore the quantity $P(1-e^{-\alpha z})$ is the power absorbed by the medium. It will be understood from the foregoing that the amount of divergence will directly indicate the absorption component of a medium which component absorbs the particular wavelength employed, while the remaining components do not. However, if fluorescence should constitute an important energy loss mechanism, then the right hand side of the foregoing equation (1) must be multiplied by a constant that is less than unity. For a medium that is a liquid, i.e., where convection is an important heat loss mechanism, the foregoing theoretical relationship will not hold, and in such case the relationship must be determined experimentally. However, the basic principles are applicable to a liquid where the beam is directed vertically through such liquid.

A preferred arrangement of apparatus for use in carrying out the invention, is that illustrated in FIG. 2. The method may be employed to detect and/or measure the presence of oil in a liquid. An important application would be for controlling the quality of ballast water that is to be discharge from ships at sea. In such case there is usually a considerable amount of solid particles in the water which would attenuate the beam. However, the effect on the method according to this invention is much less than on a method using absorbtion spectrosopy. For example, consider a medium in which a light beam would undergo a five percent attenuation due to absorption of a particular component and a five percent attenuation due to scattering of the light beam. In measuring for the component by absorption spectroscopy there would be an absorption reading of about 10 percent instead of a true value for the component only of five percent. Consequently, the error is substantial and the component might be missed. On the other hand, by employing a technique according to this invention the five percent caused by scattering would merely reduce the amount of light that would be effective in causing the absorption defocusing. Consequently the defocusing measurement of this invention would be reduced by only about five percent. Therefore, the reading would be 95 percent of what it should have been and a small amount of crude oil, for example, would be detected.

Referring to FIG. 2, there is indicated a sample 20 that includes a small amount of crude oil dissolved in carbon tetrachloride. It has been found that concentrations as low as a few parts per million will produce a measurable defocusing. There is a laser instrument 23 which emits a laser beam 24 that has a wavelength of 488.0 millimicrons. In order to control the beam power of the laser 23, there is a semi-reflecting mirror 28 that directs a portion of the beam 24 to a photodetector 29.

It will be understood that any feasible laser instrument such as one commercially available, might be employed. However, the method has been carried out using a Coherent Radiation Laboratory 52A Argon Laser.

The beam 24a continues through the mirror 28 to penetrate the sample cell 20. The sample employed provides a medium which has an absorbing component of crude oil which is dissolved in carbon tetrachloride, benzene and water. Since all three of these liquids are transparent to the laser wavelength employed, the absorption is only caused by any crude oil. Thus, depending upon the concentration of the absorbing component (i.e. crude oil) there will be a diverging angle $\partial$ caused by the self defocusing of the beam. In other words there is a diverging beam 32 which leaves the sample cell 20 and impinges upon a screen 33 where an image is created. Such image may be scaled or otherwise measured to determine the amount of divergence.

It will be appreciated that in place of the screen 33 there might be employed a plurality of photo detectors 34 which are situated in the plane of the image of the beam.

It will be noted that the component being detected is preferably one which has substantially no fluorescent properties when subjected to the laser beam. This is so because any such fluorescence tends to reduce the energy that goes into producing heat for the consequent change in refractive properties.

It will be understood that by employing the application of the laser beam vertically through the sample, the effects of having a liquid medium will not be unduly distorting in regard to the defocusing of the beam. Of course, the vertical direction of the beam through the sample might be either upward or downward.

As already noted above, this invention is especially applicable to measurement of small quantities of oil. An important application is one where prior types of measurement, such as the use of absorption spectroscopy would be quite ambiguous. Thus, as indicated above the monitoring of ballast water to be discharged from ships at sea, would be a case where there would be quite apt to be considerable solid particulate matter. Such would, of course, cause scattering and thus attenuation of the beam. But by employing this invention, such scattering effect would not invalidate the measurement. It would merely reduce the light beam intensity somewhat, while still permitting the determination concerning the presence of oil in accordance with the invention.

While a particular embodiment of the invention has been described above in considerable detail in accordance with the applicable statutes this is not to be taken as in any way limiting the invention but merely as being descriptive thereof.

I claim:

1. Method of measuring low concentrations of oil in a transparent medium, comprising
    transmitting a laser beam through said medium,
    said beam having a wavelength of about 448.0 millimicrons which is absorbed by said oil, and
    determining the amount of divergence of said beam created by passage through said medium.
2. Method according to claim 1, wherein
    said amount of divergence is determined by measuring the width of the image of said beam at a predetermined distance from said medium.
3. Method according to claim 2, wherein
    said amount of divergence measurement is made by scaling said image width on a screen.
4. Method according to claim 2, wherein
    said amount of divergence measurement is made by a plurality of photodetectors situated in the plane of said image of said beam.
5. Method of measuring low concentrations in a fluid sample of crude oil dissolved in carbon tetrachloride, benzene and water, comprising
    transmitting a beam of laser light having a wavelength of 448.0 millimicrons,
    said beam being directed vertically through said sample,
    said beam being substantially cylindrical with a predetermined width, and
    measuring the width of the image of said beam after passing through said sample at a predetermined distance therefrom by scaling said image on a screen.
6. Method according to claim 5, wherein
    said beam width measurement is made by locating a plurality of photodetectors in the plane of said image of said beam.

7. System for measuring low concentrations of oil in a transparent medium, comprising
   means for transmitting a laser beam through said medium,
   said beam having a wavelength of about 448.0 millimicrons, and
   means for determining the amount of divergence of said beam created by passage through said medium.
8. System according to claim 7, wherein
said means for determining comprises
   means for measuring the width of the image of said beam at a predetermined distance from said medium.
9. System according to claim 8, wherein
   said means for measuring the width of the image comprises a screen located at said predetermined distance.
10. System according to claim 8, wherein
   said means for measuring the width of the image comprises a plurality of photo detectors located on a plane at said predetermined distance.

* * * * *